United States Patent [19]

Michaels et al.

[11] Patent Number: 4,595,002
[45] Date of Patent: Jun. 17, 1986

[54] NEBULIZER

[75] Inventors: Thomas L. Michaels, Wonder Lake; Michael J. Finley, Park City; Robert A. Virag, Cary, all of Ill.

[73] Assignee: Baxter Travenol Laboratories, Inc., Deerfield, Ill.

[21] Appl. No.: 544,023

[22] Filed: Oct. 20, 1983

[51] Int. Cl.$^4$ .............................. A61M 11/02
[52] U.S. Cl. ................... 128/200.21; 128/205.11; 222/153; 222/553; 261/DIG. 65
[58] Field of Search .............. 128/200.18, 200.21, 128/205.11, 205.24, 203.25; 222/153, 553; 261/DIG. 65

[56] References Cited

U.S. PATENT DOCUMENTS

| | | | |
|---|---|---|---|
| 733,027 | 7/1903 | Goldan | 128/203.25 |
| 2,593,134 | 4/1952 | Gibbon | 128/200.21 |
| 2,778,617 | 1/1957 | Gibbon | 261/19 |
| 2,847,248 | 8/1958 | Schmitt et al. | 239/338 |
| 3,724,454 | 4/1973 | Brown | 128/200.21 |
| 3,836,079 | 9/1974 | Huston | 239/74 |
| 3,857,909 | 12/1974 | Huggins | 261/64 R |
| 3,906,996 | 9/1975 | DePass et al. | 137/604 |
| 3,913,607 | 10/1975 | Price | 137/271 |
| 3,915,386 | 10/1975 | Vora | 239/338 |
| 3,977,432 | 8/1976 | Vidal | 137/604 |
| 4,039,639 | 8/1977 | Kankel et al. | 261/121 R |
| 4,190,046 | 2/1980 | Virag | 128/200.21 |
| 4,195,044 | 3/1980 | Miller | 261/142 |
| 4,267,974 | 5/1981 | Kienholz et al. | 239/74 |
| 4,291,838 | 9/1981 | Williams | 239/138 |
| 4,299,355 | 11/1981 | Hakkinen | 239/338 |

Primary Examiner—Henry J. Recla
Attorney, Agent, or Firm—Paul C. Flattery; John A. Caruso; Kay H. Pierce

[57] ABSTRACT

A nebulizer is provided which includes a liquid container and a cap attachable thereto. The cap includes a outlet port for delivery of a nebulized liquid/gas mixture to a patient, a gas inlet, a venturi in communication with the gas inlet, a conduit through which liquid may be circulated in the cap and heated by an external heater, a liquid outlet adjacent the end of the venturi, so that the gas flowing through the venturi draws out the liquid, and a dial rotatable on the cap. The dial has windows which may be positioned over openings in the cap to allow air from the environment to enter the cap and dilute the gas to a desired concentration. The dial engages the cap securely once its position is set on the cap, so the gas concentration is not inadvertently changed during use of the nebulizer.

1 Claim, 10 Drawing Figures

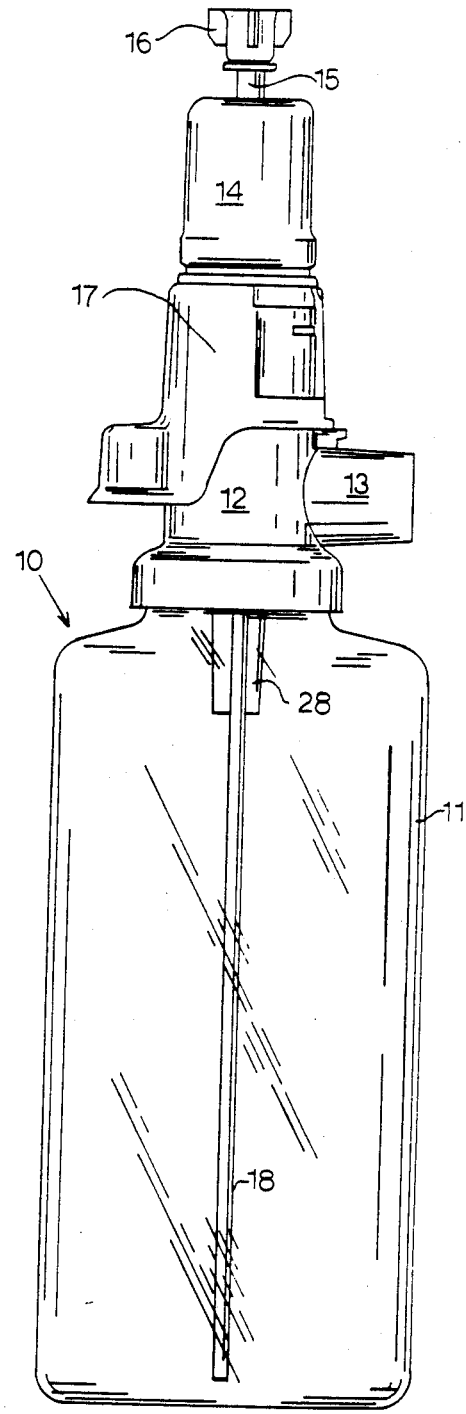
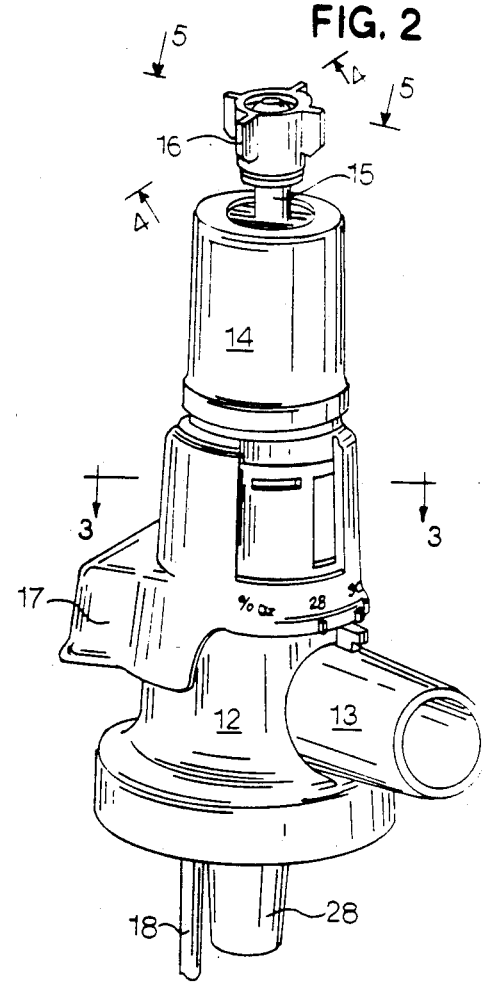
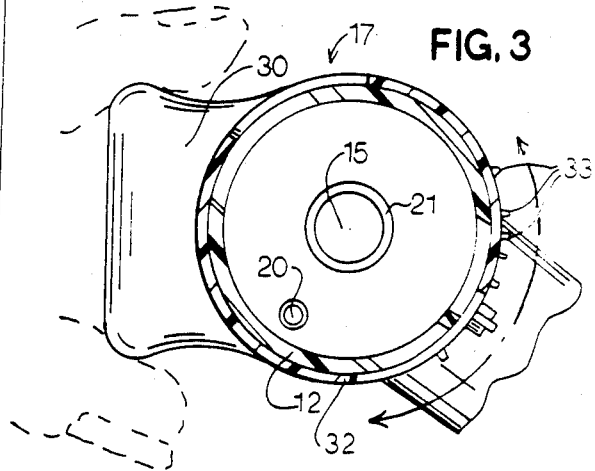

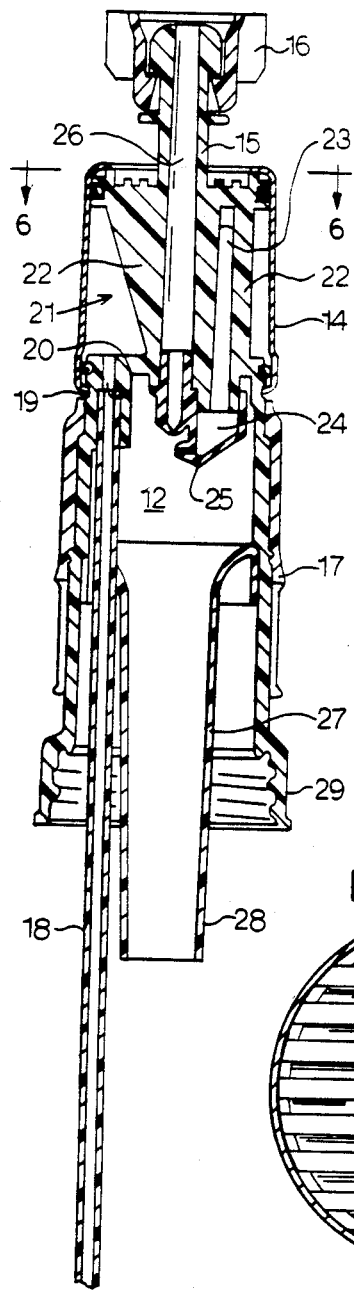
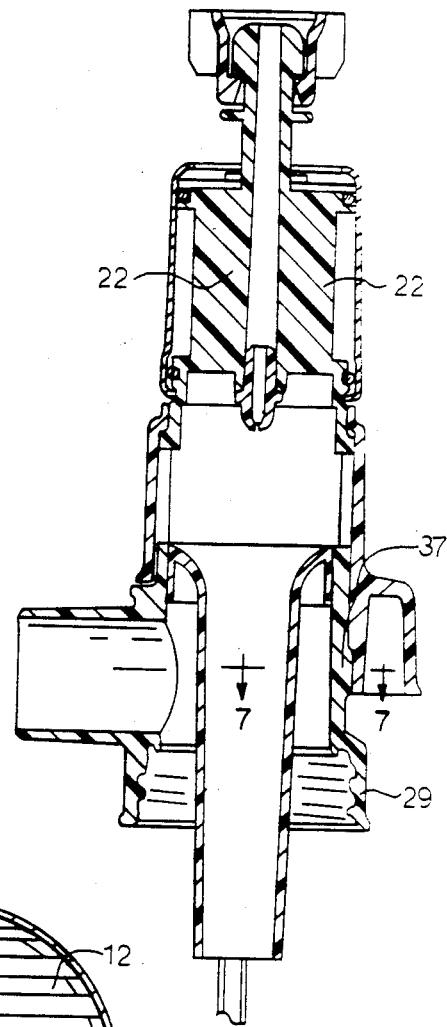
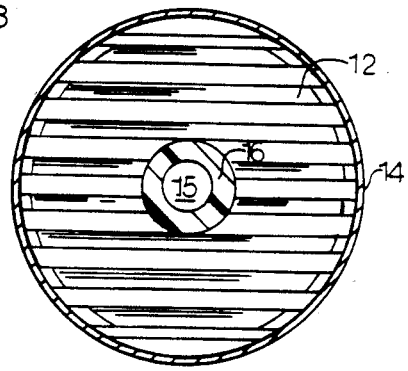
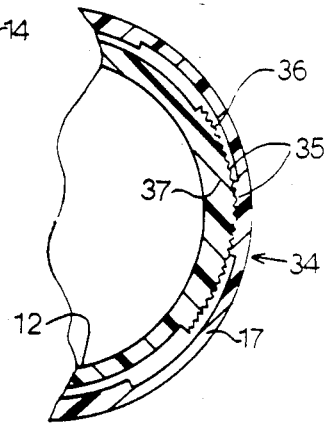

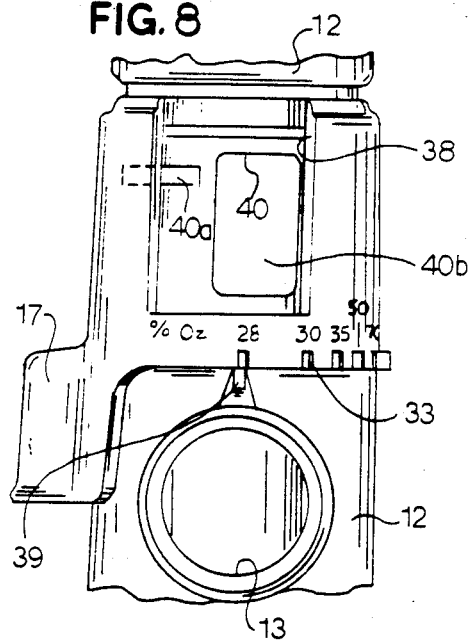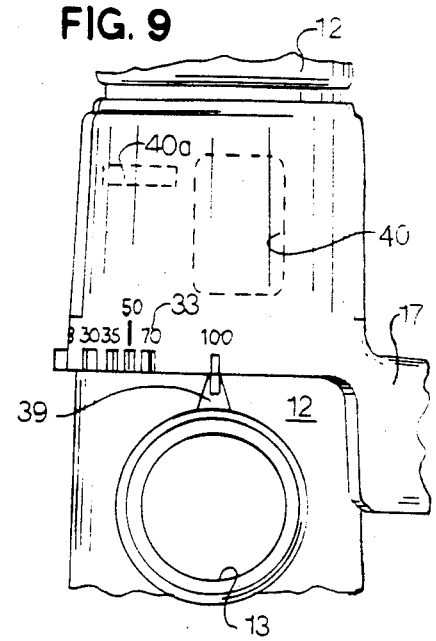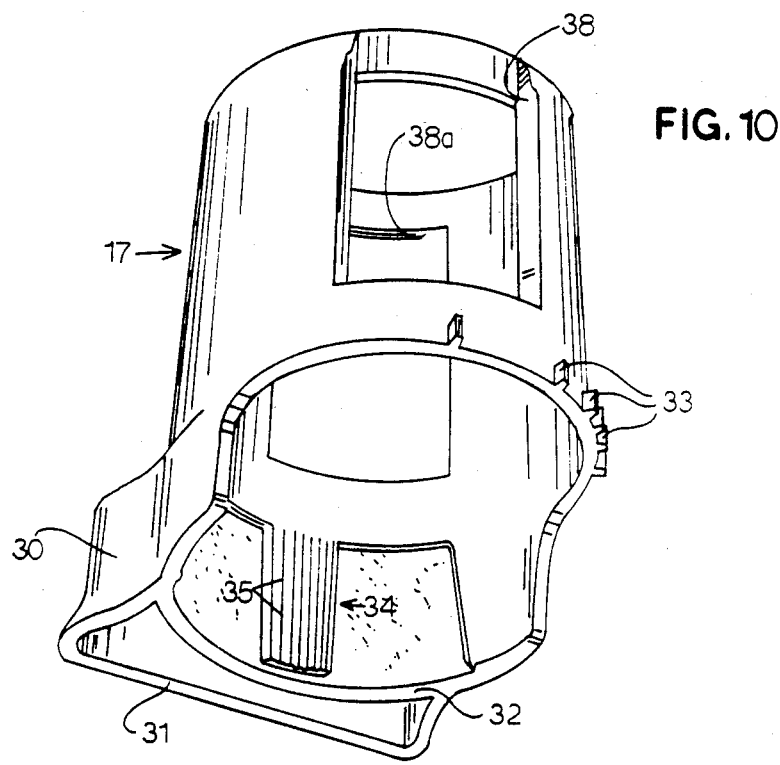

NEBULIZER

BACKGROUND OF THE INVENTION

This invention relates to a nebulizer. More particularly it relates to a nebulizer having means by which the percentage of a gas, preferably oxygen, in a nebulized liquid/gas mixture can be easily controlled.

Nebulizers are used for various respiratory therapy treatments, particularly providing humidification to the lungs to make breathing easier and often as a vehicle for delivering medication deep into the lungs. In connection with oxygen therapy, oxygen is passed through a venturi in the nebulizer, is mixed with a nebulized liquid, and the mixture is then propelled at a high velocity out of the nebulizer to the patient. Simultaneously, while the nebulized liquid/oxygen mixture is delivered to the patient, the non-nebulized, larger liquid droplets settle back into the liquid storage. To increase the oxygen carrying capacity of the liquid, the liquid is preferably heated before nebulization. This type of nebulizer is described in U.S. Pat. No. 4,190,036.

Although this prior art nebulizer is satisfactory, improvements provided by the present nebulizer eliminate some of the former nebulizer's disadvantages. For instance, the present invention provide means for more accurately controlling the oxygen dilution in the nebulized mixture, for eliminating large particle spit-out of any non-nebulized liquid into the pathway leading to the patient, for more positively maintaining the user's initial selection of the oxygen concentration, and for eliminating uneven or non-uniform heating of the liquid prior to it being mixed with the oxygen for delivery to the patient.

SUMMARY OF THE INVENTION

In accordance with this invention, a nebulizer is provided which includes a container for holding a liquid to be nebulized and a cap having means for being attached to the container.

A dip tube is carried in the cap in a position by which it extends into the container when the cap is attached to the container. One end of the tube extends into the container so liquid stored therein can be drawn up the tube, while the other end of the tube is in flow communication with conduit means in the cap by which the liquid drawn in the cap circulates through and around the cap, so it can be heated. The conduit means leads from the dip tube and communicates with a liquid outlet. As the liquid flows into the outlet, a gas, preferably oxygen, is delivered into the cap through a gas inlet. The gas moving at a high velocity through a venturi draws the liquid out of the liquid outlet and nebulization of the liquid/oxygen mixture occurs.

A thin metal heat exchange cylinder may be positioned over the upstanding portion of the cap surrounding the channels of the conduit means. By heating of the metal shell, the liquid passing through the conduit means is heated to provide a supply of warm liquid to the outlet of the venturi. Preferably, a toroidal or ring-shaped heater is provided around the metal heat exchanger cylinder, so that heating contact between the heater and liquid passing through the conduit means is directly through the thin metal of the cylinder.

Further, the nebulizer includes an oxygen/air mixture control dial, which surrounds the cap for controlling the concentration of the oxygen in the oxygen/air mixture being delivered to the patient. The cap further includes an opening by which air from the environment may be brought into proximity with the venturi, so that the desired oxygen concentration occurs to affect a desired oxygen/air mixture. Provided on the dial are means which cooperate with means on the cap for maintaining the dial in the position selected by the user once the dial is set. By rotating the dial on the cap, a window in the dial can be placed over an opening in the cap, whereby air from the environment may enter the cap to dilute the oxygen. The amount of shading of the opening in the cap by the window in the dial is automatically determined by oxygen dilution values marked on the dial and by the user's setting of the dial.

The nebulizer cap and container may be disposable, while the heater will be reuseable. An object of this invention is to provide a nebulizer having precise oxygen/air mixture setting controls which are not inadvertently changed during operation of the nebulizer and having the ability to provide for a lower percentage of oxygen in the mixture than is now known or capable of being delivered by presently used nebulizers. Particularly, it is desired and accomplished by this invention that the nebulizer may entrain a sufficient quantity of air to dilute the oxygen flowing through the venturi to a concentration of about 28%.

BRIEF DESCRIPTION OF THE DRAWINGS

FIG. 1 is a perspective view of the nebulizer of the present invention.

FIG. 2 is a perspective view of particularly the cap of this nebulizer.

FIG. 3 is a cross sectional view of this nebulizer taken along lines 3—3 of FIG. 2.

FIG. 4 is a cross sectional view of this nebulizer taken along lines 4—4 of FIG. 2.

FIG. 5 is a cross sectional view of this nebulizer taken along lines 5—5 of FIG. 2.

FIG. 6 is a cross sectional view of this nebulizer taken along lines 6—6 of FIG. 4.

FIG. 7 is a cross sectional view of this nebulizer taken along lines 7—7 of FIG. 5.

FIG. 8 is a perspective view of particularly the cap of this nebulizer showing one setting of the dial on the cap.

FIG. 9 is a perspective view of particularly the cap of this nebulizer showing another setting of the dial on the cap.

FIG. 10 is a perspective view of the dial of this nebulizer.

DESCRIPTION OF THE PREFERRED EMBODIMENTS

Referring to FIG. 1, a nebulizer, generally indicated at 10, is shown. The nebulizer includes a container 11, which is prefilled with the liquid component of the gas/liquid mixture to be nebulized. Attached to the container is a cap 12 having a outlet port 13 by which the nebulized mixture can be delivered to the patient. An upstanding portion of the cap, which is described in more detail below with respect to other drawings, is covered by a thin metal heat exchange shell 14. Protruding out from the top of the cap is an oxygen inlet 15 having a screw cap 16 for attachment to an oxygen delivery system (not shown), so that oxygen may be delivered into cap 12. Surrounding the lower portion of cap 12 is an oxygen/air mixture control dial 17.

Turning now to FIGS. 4 and 5, a dip tube 18 has an upper end 19 inserted into an opening 20 of the upper portion of cap 12. Opening 20 extends through and into the uppermost portion of cap 12, which uppermost portion defines a pathway or conduit means 21 through which the liquid may be circulated. As shown in FIGS. 4 and 5, the conduit means includes several vanes 22 around which the liquid flows, so that it may be heated by contact with shell 14 when a heater (not shown), such as a toroidal heater, is placed around the shell.

After circulation of the liquid around the vanes 22, the liquid is drawn into an open ended cylinder 23 defined in the cap, which communicates with a passageway 24 that serves as a liquid outlet into a nebulizer venturi 25.

To create the oxygen/liquid mixture which will be nebulized and delivered to the patient, oxygen delivered into inlet 15 passes through a port 26 and is accellerated by the conventional constriction of venturi 25. The rush of oxygen across passageway 24 creates a suction, so that liquid in cylinder 23 is drawn downwardly, passing through passageway 24, and through venturi 25, whereby nebulization of the oxygen/liquid mixture occurs. Thereafter, the oxygen/liquid mixture which has been nebulized rushes downwardly and through the open outlet port 13 and is delivered to the patient. Any large, un-nebulized liquid droplets are not delivered to the patient, but instead fall downwardly through open ended chamber 27 back into the liquid storage in container 11. The lower end 28 of chamber 27 is sized so that it extends downwardly into container 11 past the neck of the container, which is approximate the screw thread attachment areas 29 of cap 12 when the cap is attached to the container.

With the prior art nebulizer, the chamber did not extend actually into the container, but only extended down as far as the neck. This creates some problem because the large, un-nebulized droplets are carried along with the nebulized mixture, rather than being dropped back into the container. The narrow area of the neck portion of the container contributes to the high velocity of the mixture at that point to cause the droplets to be carried along with the nebulized mixture, whereas with the chamber of the present invention, since it extends down into the container where the area is larger, the nebulized mixture has a lower velocity and the large unnebulized particles are not carried along with the nebulized mixture.

Turning particularly to dial 17, it is best shown in FIG. 10. The dial fits around cap 12 and has several portions. The base of the dial includes an outwardly extending squeezable hand grip 30. The hand grip is essentially formed by a outer wall 31, which is integral with a primary wall 32 that extends around the dial. On the outer surface of the lower portion of wall 32 are graduation marks 33. On the inner surface of the lowermost portion of wall 32 is a cap engaging means 34. In the embodiment shown means 34 are a series of ridges 35, which are best shown in FIG. 7. The ridges engage similar ridges 36 on a dial engaging means 37 of cap 12. Thus, once the dial is set, the engagement of the ridges on the cap and dial prevent any inadvertant movement of the dial to change the concentration of oxygen delivered through the nebulizer. Finally, in the uppermost portion of dial 17, essentially opposite one another, are two windows 38 and 38*a*, which are formed by surrounding portions of the dial.

Now turning to the operation of the dial to create a particular oxygen dilution, in FIGS. 8 and 9 two different positions of dial 17 on cap body 12 are illustrated. In FIG. 8, there is a marker 39 on cap body 12. By gripping hand grip 30 with the fingers, as shown in FIG. 3, ridges 35 and 36 of the dial and cap are disengaged and the dial may be rotated around the cap to a selected position. As shown in the drawings, oxygen dilution values are printed on the dial above graduation marks 33, so that the user can align the dilution values with marker 39 to obtain the oxygen dilution desired.

Oxygen dilution in this nebulizer is affected by the mixture of air from the environment with oxygen being brought into the nebulizer through inlet 15. Note particularly in FIGS. 8 and 9 that openings 40, 40*a* and 40*b* are provided in cap body 12. By rotation of dial 17 on the cap, these openings are either exposed, exposed partially, or not exposed to the outside environment so that air may enter through them and be mixed with the oxygen being delivered into the nebulizer. As shown in FIG. 8, when the dial is rotated and window 38 overlies opening 40 and at least a part of opening 40*a*, and window 38*a* overlies opening 40*b* enough air would be allowed to enter these openings and be mixed with the oxygen being delivered into the nebulizer to affect a 28 percent concentration of such oxygen, which corresponds to the marking "28" indicated on dial 17 above cap marker 38. However, if the dial is rotated further, such as shown in FIG. 9, neither window 38 or 38*a* overlies opening 40, 40*a* or 40*b* in cap 12 and no air is allowed to enter into the interior of the cap to dilute the oxygen being delivered, which means essentially that the oxygen concentration is 100%, as shown in that figure.

A particular advantage of the nebulizer of this invention over prior art nebulizers such as the one discussed above is that it allows for a maximum amount of air to be drawn into the interior of the cap for mixing with the oxygen being delivered to the nebulizer, so that a low concentration of oxygen can be mixed with the liquid to be nebulized. This is possible because, contrary to the prior art nebulizer discussed above, the flow path of air from the environment into the nebulizer is directly at the point where the oxygen enters the nebulizer and is not off at a right angle. It is within the scope of this invention that other configurations of windows 38 and openings 40 can be provided.

These and other alternatives to the embodiments discussed above can be made within the scope of this invention.

What is claimed is:

1. A nebulizer, adapted to provide to a patient a nebulized mixture of a gas and a liquid, comprising:

a container for holding the liquid, said container having a neck;

a cap removably attached to said neck of said container, said cap having a dip tube, a liquid outlet, a first air inlet opening and a venturi passage, said dip tube extending into said container for withdrawing liquid from said container into said liquid outlet in said cap, said cap further having conduit means in communication with said liquid outlet and also in communication with said venturi passage in said cap, said cap further including a gas inlet in communication with said conduit means to accelerate gas in said conduit means past said liquid outlet and said air inlet and into said venturi passage to create a suction to draw liquid in said dip tube into said venturi passage to create said nebulized mixture of gas and liquid, said cap further having an outlet port for delivering said nebulized mixture to said patient;

dial means including a cylindrical primary wall having an inner surface mounted around said cap and having a second air inlet opening rotatable over said first air inlet opening to vary the size thereof, said dial means for controlling the concentration of air aspirated into said mixture, the position of said dial affecting a desired gas concentration; and maintaining means for maintaining the position of said dial on said cap so that the position of said dial on said cap and said gas concentration is not inadvertently changed during operation of said nebulizer, said means including an outwardly extending squeezable hand grip disposed on said primary wall, said grip including an outer wall which extends generally parallel with said primary wall and opposite side walls which extend generally perpendicular to said outer wall and connecting said outer wall to said primary wall, said maintaining means being disengagable by the application of pressure on said opposite side walls of said grip, said maintaining means including at least two engagement ridges on said inner surface of said primary wall directly between said opposite side walls and at least one mating ridge on said cap for disengagable engagement with said engagement ridges in which squeezing said hand grip on said opposite side walls will cause said primary wall between said opposite side walls and therefore, said engagement ridges to move away from said mating ridge on said cap to allow said dial to be selectively rotated on said cap.

* * * * *